Figure 1:
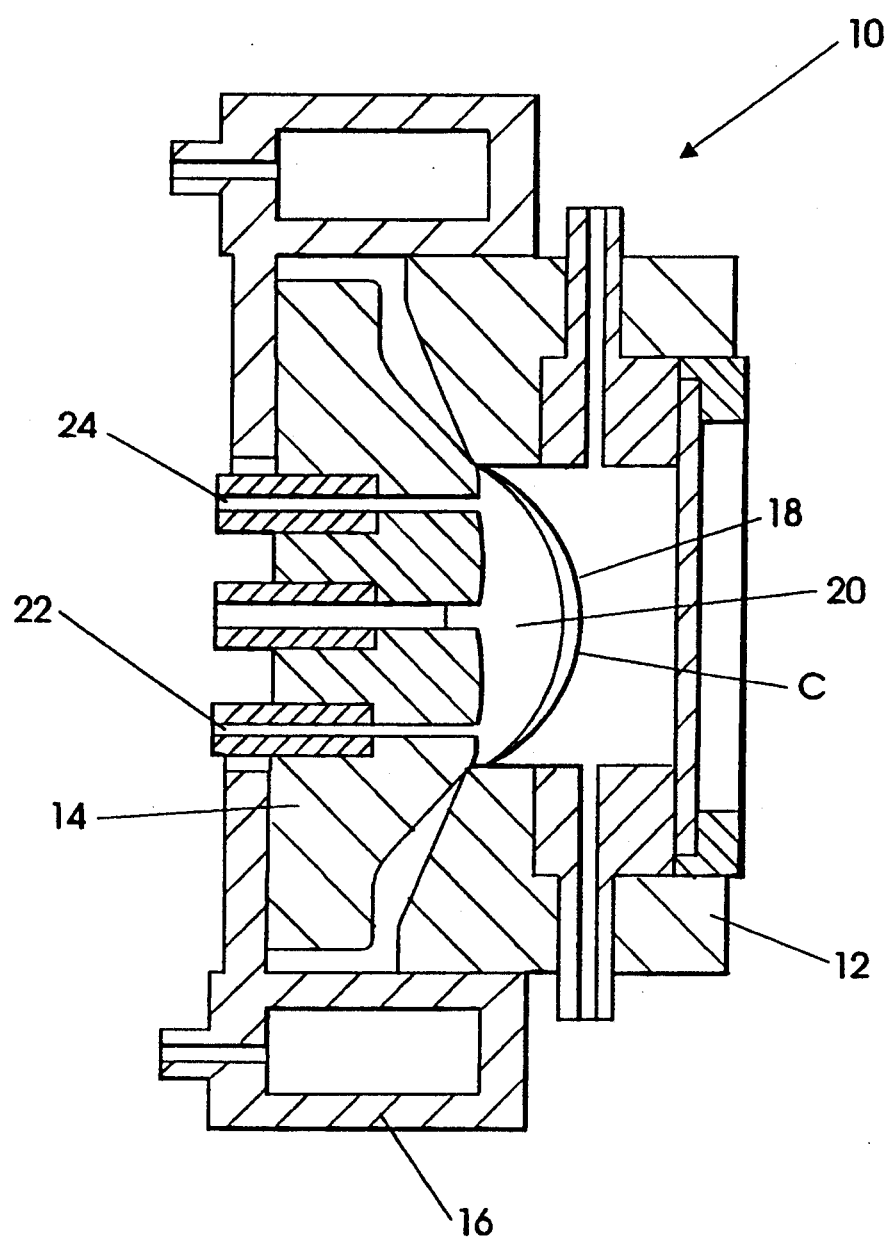

United States Patent [19]
Andermann

[11] Patent Number: 5,380,537
[45] Date of Patent: Jan. 10, 1995

[54] SINGLE IRRIGATING SOLUTION USED IN OCULAR THERAPY FOR THE ENDOTHELIUM PROTECTION AND CORNEA PRESERVATION

[76] Inventor: Guy Andermann, 2, Rond Point de l'Esplanade, F, 67000 Strasbourg, France

[21] Appl. No.: 982,222
[22] Filed: Nov. 25, 1992

Related U.S. Application Data

[63] Continuation of Ser. No. 634,498, Dec. 27, 1990, abandoned.

[30] Foreign Application Priority Data

Dec. 29, 1989 [FR] France .................. 89 17547

[51] Int. Cl.⁶ .............. A61K 33/00; A61K 33/42; A61K 33/14; A61K 33/06
[52] U.S. Cl. .................. 424/602; 424/605; 424/677; 424/681; 424/717; 514/912
[58] Field of Search .............. 514/912; 424/602, 605, 424/677, 681, 717

[56] References Cited

U.S. PATENT DOCUMENTS

| | | | |
|---|---|---|---|
| 4,443,432 | 4/1984 | Garabedian et al. | 424/127 |
| 4,550,022 | 10/1985 | Garabedian et al. | 424/127 |
| 4,620,979 | 11/1986 | Schachar | 424/153 |
| 4,649,050 | 3/1987 | Veech | 424/153 |
| 4,663,289 | 5/1987 | Veech | 435/240 |
| 4,837,021 | 6/1989 | Andermann et al. | 424/602 |
| 4,952,573 | 8/1990 | LeClerc et al. | 514/311 |
| 5,116,868 | 5/1992 | Chen et al. | 514/546 |

FOREIGN PATENT DOCUMENTS 8600228 1/1986 European Pat. Off. .

OTHER PUBLICATIONS

"Rhesus monkey aqueous humor composition and a primate ocular perfusate", Douglas E. Gaasterland, Jonathan E. Pederson, Helen M. MacLellan, and Venkat N. Reddy, Invest. Opthalmol. Visual Sci., Nov. 1979, vol. 18, No. 11, pp. 1139–1150.

Dikstein, et al., "Corneal Endothelial Pumping in the Presence of Insulin and GABA," Exp. eye Res. (1980) 31, 239–241.

Primary Examiner—Zohreh Fay
Attorney, Agent, or Firm—Robert G. Rosenthal

[57] ABSTRACT

An irrigating solution used during ocular surgery for endothelium protection and corneal preservation is disclosed. The solution is stored in a single container and mixing prior to use is not required.

30 Claims, 2 Drawing Sheets

SINGLE IRRIGATING SOLUTION USED IN OCULAR THERAPY FOR THE ENDOTHELIUM PROTECTION AND CORNEA PRESERVATION

This is a continuation of copending application Ser. No. 07/634,498 filed on Dec. 27, 1990 now abandoned.

FIELD OF THE INVENTION

This invention relates generally to the field of ocular surgery and more specifically to solutions used during surgery to preserve the endothelium and protect the cornea.

BACKGROUND OF THE INVENTION

It has been demonstrated for some time that ocular surgery of the anterior and posterior segments of the eye seriously affect the integrity of the corneal endothelium. The trauma to which the endothelial cells are subjected shows up in an increase in the thickness and a more or less significant opacification of the cornea.

In view of the damage sustained, the search was undertaken for solutions that prevent the irreversible destruction of the cells of the endothelial layer.

Ocular irrigation, necessary during these surgical procedures on the ocular sphere, has progressed step by step, began the use of sterile isotonic saline solutions.

Because the use of such solutions proved likewise to have a toxic effect, for a time the use of the Lactate-Ringer solution, which had previously served for the irrigation of other tissues of the organism, was preferred. However, it rapidly became apparent that the significant variations in pH to which this solution was subject were not suited to the maintenance of corneal integrity.

In the early 60's, a solution containing the ions essential for the maintenance of the endothelial pump ($Ca^{++}$, $Mg^{++}$, $K^+$, $Na^+$) was marketed under the name B.S.S. This mixture represented a significant advance although it was subsequently determined to be the cause of corneal edemas because of its nonphysiological composition.

Indeed, only a mixture imitating perfectly the composition of the aqueous humor is capable of causing minimal damage to the cells of the endothelium.

For this reason, an improved mixture containing glucose, sodium bicarbonate and oxidized glutathione was subsequently described in U.S. Pat. Nos. 4,443,432 and 4,550,022.

This mixture offers the advantage of being closer to the composition of human aqueous humor, containing, in addition to the essential ions described above, a physiological buffer (bicarbonate), glucose, providing energy and an antioxidant (oxidized glutathione).

The superior efficacy of this solution was demonstrated in vitro, specifically on the recovery time for the transparency of the cornea on the one hand, and the intercellular junctions on the other.

However, this preparation presents several disadvantages, specifically in its daily use. Indeed, it is an extemporaneous preparation packaged in two parts. At the time of use by the surgeon, the contents of the first container containing calcium chloride, magnesium chloride, and the oxidized glutathione, are brought into contact with the contents of the second container containing the other ions, the sodium bicarbonate, and the sodium phosphate. This form, although inconvenient for the user, permits storage of the mixture in a form that prevents solution incompatibility and the precipitation of calcium carbonate. Indeed, ocular irrigation solutions must be clear, without any suspensions or particles. The two part solution thus allows for a stability limited to 6–8 hours after preparation.

It is, therefore, apparent that this preparation is difficult to make, which leads to high production costs and consequently to a high final product cost. Its use likewise involves other significant disadvantages such as the possibility of microbial contamination during the preparation of the final mixture. Users (surgeons and para-medical personnel) can likewise forget to make the mixture, which would be detrimental to the maintenance of the corneal integrity because of an inadequate pH in the first solution being mixed with the second solution.

On the other hand, the absence of lactic acid in the mixture distances it from the definition of the perfect physiological solution. Indeed, aqueous humor and the vitreous humor contain lactate ions in a significant quantity.

It has now been discovered that it was possible to mix, in a single solution, all the elements (or their structural analogues) without exception of the liquids bathing the cornea on the one hand and the retina on the other.

Indeed, by modifying the concentration of certain elements such as the phosphates, the precautions at the point of the making of the mixture, the improvement of certain stages of the manufacturing process, and the replacement of the oxidized glutathione by a structural analogue, have allowed the industrial production of a stable, efficient, and economically advantageous composition.

These modifications and improvements involve specifically:

The decrease in the phosphate concentration;

The saturation of the solution with carbon dioxide, which has the effect of avoiding the precipitation of calcium carbonate;

The use of organic counter ions of calcium (such as glucoheptonic acid, for example) instead of calcium chloride;

The replacement of the glucose, fragile to heat sterilization, with other suppliers of cellular energy, like biological acids, such as fumaric acid, succinic acid, citric acid and their pharmaceutically acceptable salts, such as in the formula (with n between 1 and 3):

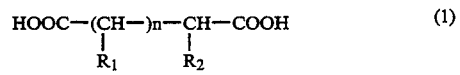
(1)

in which:
$R_1$ is a hydrogen atom or an —OH hydroxyl,
CH—$R_1$ may be replaced with a radical C=O
$R_2$ is a hydrogen atom or an —OH hydroxyl, the carbon-carbon link is a single or double link;
the replacement of the glucose by complex sugars such as gluconic acid, glucoheptonic acid, glucono-glucoheptonic acid for example, and their salts;
the mixture with the structural analogues of reduced glutathione, like, for example, gamma amino butyric acid (GABA) or its gabaergic structural analogues, as well as its pharmaceutically acceptable salts, as in the formula (with n between 1 and 5):

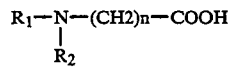

in which:
- $R_1$ is a hydrogen atom or an inferior straight chain alkyl group, having from 1 to 3 carbon atoms, and including, for example, methyl, ethyl and propyl radicals, and
- $R_2$ is a hydrogen atom or an inferior straight chain alkyl group, having from 1 to 10 carbon atoms, or a $-NH_2$ radical, and including, for example, methyl, ethyl and propyl radicals.

Among the typical compounds represented by formula (2) and useful as active compounds in the ocular irrigation mixtures according to the present invention, can be listed, as non exhaustive examples, the following compounds: aminocaproic acid, glycocoll, dimethylglycine, sarcosine, the association with the monoacids, like lactic acids and its pharmaceutically acceptable salts).

These modifications lead to a perfectly clear solution, which can be sterilized with dry or moist heat. These procedures of sterilization by dry or moist heat lead to a sterile and apyrogenic solution, which is one of the essential characteristics of such a composition.

In addition to these compounds useful in the efficacy of the composition, of primary concern is the addition of mineral salts such as sodium chloride, potassium chloride, magnesium chloride, sodium bicarbonate, in quantities sufficient to form an isotonic and stable aqueous solution. The purpose of these elements is to create a favorable physiological medium which imitates the composition of natural aqueous humor.

Furthermore, the new composition allows the achievement of a solution whose extreme pH values do not vary within the limits of 6.8 and 7.6. The osmolarity of these solutions is between 290 and 310 mOsm.

All of these characteristics allow the insurance of the formulation of the composition as close as possible to physiological aqueous humor.

The pre-clinical and clinical results appearing below show the superiority of the product of the invention over the reference products, like the BSS solution, for example, or the Lactate-Ringer solution.

The compounds described in this invention were recognized as playing a role in the protection and the preservation of the cornea during surgical procedures in the ocular sphere. These compounds, associated with a compound that provides energy to the cells like glucoheptonic acid, for example, or lactic acid, and with mineral ions have shown a remarkable deturgescent effect on the corneal endothelium.

Figure 2:
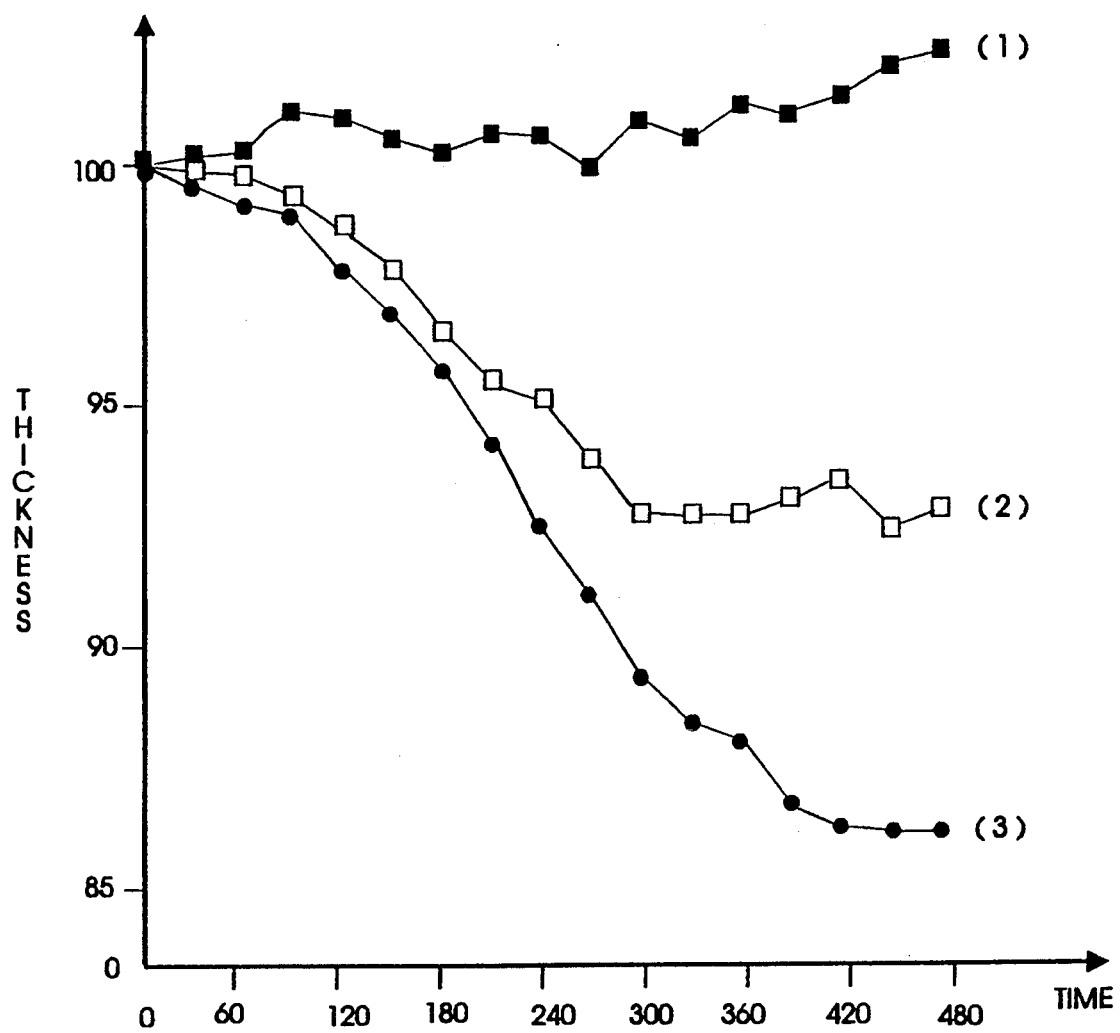

In reference to the drawings, as hereinafter discussed, FIG. 1 is a cross-sectional, elevation view of a perfusion cell, utilized for testing of the irrigating solution of the present invention, and FIG. 2 is a graph of change of thickness of the cornea, as a function of time in minutes, for saline solution (line 1), a solution associating mineral salts, calcium salt of glucoheptonic acid and gama aminobutyric acid (line 2), and a composition according to the present invention (line 3).

The invention will be better understood through the following non exhaustive examples. They involve both the mixtures according to the invention and series of tests in vitro and in vivo using one or another example of the invention.

Example of Preparation

| | |
|---|---|
| Gamma amino butyric acid | 0.10 mg % to 10 mg % |
| Potassium chloride | 3.5 mg % to 50 mg % |
| Calcium glucoheptonate | 4.6 mg % to 80 mg % |
| Magnesium chloride (hexahydrate) | 1.5 mg % to 45 mg % |
| Sodium bicarbonate | 200 mg % to 300 mg % |
| Sodium acid phosphate (dihydrate) | 2.0 mg % to 8.0 mg % |
| Sodium lactate | 25 mg % to 150 mg % |
| Sodium chloride | 500 mg % to 800 mg % | each of the quantities being expressed in weight/volume.

The effectiveness of the above referenced composition was studied from the point of view of its therapeutic activity in vitro and in vivo:

In Vitro Tests with the Bovine Cornea

Eyes were removed from bovines immediately after slaughter and were forwarded as rapidly as possible to the testing laboratory where the cornea were removed before being pre-distended in plexiglass perfusion cells. After two hours, the cornea had, thus, acquired a thickness of 800 to 900 microns.

The perfusion cells generally indicated at 10 were made of two half-cells 12,14 held against each other by a jacket of thermostable aluminum 16. This arrangement allowed the clamping of a cornea C by means of a sclerotic crown 18 of 5 mm.

The endothelial compartment 20 was continuously perfused by means of a peripheric tube 22 which brought the tested solutions to the endothelium. A second tube 24 diametrically opposite allowed the perfusate to evacuate. FIG. 1 is a general drawing of the device.

A thermostated bath allowed the maintenance of a temperature of 37 degrees C. inside the perfusion cell. Repeated measurements of the corneal thickness were made throughout the perfusion experiment with a Haag-Streit slit-lamp equipped with a pachymeter.

The experiment compared the corneal deturgescence during six hours of contact with a saline solution on the one hand and with a solution containing a compound that provides energy to the cells (soluble salt of glucoheptonic acid) on the other, and the test solution whose composition is shown above. FIG. 2 shows that the solution at 0.9 g % sodium chloride causes no deturgescence of the cornea graph 1. On the contrary, the cornea continues to swell while the solution associating mineral salts, calcium salt of glucoheptonic acid, sodium salt of lactic acid and gamma amino butyric acid, allows a corneal deturgescence after the second hour graph 2. The maintenance of this function of "epithelial pump" continues until the sixth hour. The maximum effectiveness is, however, obtained with the solution containing a lactic acid salt, a calcium salt glucoheptonic acid, of sodium bicarbonate, and gamma amino butyric acid, following the composition described above graph 3.

Tests in Vivo on Man

Clinical tests undertaken were performed on a large number of patients by comparing the effectiveness of the solution according to the example described above with a control solution (BSS). Both products were used during surgical procedures on the ocular sphere. Tests were conducted according to the double blind method on 80 patients of both sexes. The test protocol used the endothelial cell count with a specular microscope, as well as the measurement of the corneal thickness in order to evaluate the therapeutic effectiveness of the products tested. These two objective evaluation parameters were checked before and after the surgical procedure. The statistical analysis of the results allowed the conclusion to be drawn that the solution of the invention allowed a significantly higher reduction of the percentage of cell loss (in comparison with the reference product) during the surgery performed. The results were especially significant in very long surgical procedures where the product tested, whose composition is given above, proved superior to the control product (BSS).

That which is claimed is:

1. A one-part aqueous intraocular irrigation solution characterized by a storage stability for extended periods of time greater than 24 hours without precipitation at ambient conditions and comprising:

(a) from 0.0001 grams per deciliter to 0.010 grams per deciliter of at least one gabaergic derivative having the general formula:

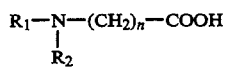

wherein:

n is from 1 to 5:

$R_1$ is hydrogen or $C_1$-$C_3$—straight chain alkyl;

$R_2$ is hydrogen or $C_1$-$C_{10}$—straight chain alkyl;

(b) from 0.0046 grams per deciliter to 10 grams per deciliter of an organic calcium salt of a non-heat labile complex sugar providing a source of energy compatible in aqueous solution with sodium bicarbonate; and (c) from 0.001 grams per deciliter per deciliter to 10 grams per deciliter of an organic acid having the general formula:

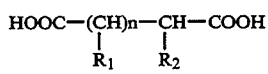

wherein:

n is between 1 and 3;

$R_1$ is a hydrogen atom of a hydroxyl group;

CH—$R_1$ may be replaced with C=O;

$R_2$ is a hydrogen or a hydroxyl;

the segment

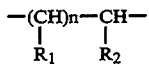

can be saturated or unsaturated; or lactic acid; or a pharmaceutically acceptable salt thereof;

(d) sodium chloride, potassium chloride, magnesium chloride, sodium bicarbonate, and sodium phosphate, in sufficient quantity to form an isotonic and stable aqueous solution.

2. The one-part aqueous intraocular irrigation solution according to claim 1 further including carbon dioxide in sufficient quantity to saturate the solution.

3. A therapeutic mixture according to claim 1 wherein the gabaergic derivative is aminocaproic acid, glycoll, dimethylglycine, sarcosine or gamma amino butyric acid.

4. A therapeutic mixture according to claim 1 wherein the acid specified under (c) is lactic acid or one of its pharmaceutically acceptable salts.

5. A therapeutic mixture according to claim 1 wherein the solution is clear, stable under heat, sterile, and apyrogenic.

6. A therapeutic mixture according to claim 1 wherein its pH is between 6.8 and 7.6.

7. A therapeutic mixture according to claim 1 wherein the osmolarity of the solution is between 290 and 310 mOsm.

8. A one part intraocular irrigation solution according to claim 1 wherein $R_1$ in the formula under (a) is a $C_1$-$C_3$ alkyl group.

9. A one part intraocular irrigation solution according to claim 1 wherein $R_2$ in the formula under (a) is an $C_1$-$C_{10}$ alkyl group.

10. An irrigation solution according to claim 1 comprising gamma aminobutyric acid, a lactic acid salt, the calcium salt of glucoheptonic acid and sodium bicarbonate.

11. An irrigation solution according to claim 1 wherein the complex sugar is gluconic acid, glucoheptonic acid or glucono-glucoheptonic acid.

12. A one-part aqueous intraocular irrigation solution according to claim 1, wherein the storage stability is at least 30 months.

13. A one-part aqueous intraocular irrigation solution according to claim 10, wherein said storage stability is at least 30 months.

14. A one-part aqueous intraocular irrigation solution characterized by a storage stability for extended periods of time greater than 24 hours without precipitation at ambient conditions and comprising:

| | | |
|---|---|---|
| Gamma amino butyric acid | 0.10 mg % to | 10 mg % |
| Potassium chloride | 3.5 mg % to | 50 mg % |
| Calcium glucoheptonate | 4.6 mg % to | 80 mg % |
| Magnesium chloride (hexahydrate) | 1.5 mg % to | 45 mg % |
| Sodium bicarbonate | 200 mg % to | 300 mg % |
| Sodium acid phosphate (dihydrate) | 2.0 mg % to | 8.0 mg % |
| Sodium lactate | 25 mg % to | 150 mg % |
| Sodium chloride solution | 500 mg % to | 800 mg % | each of the quantities being expressed in milligrams per deciliter, and wherein the pH of the solution is between 6.8 and 7.6 and the osmolarity is between 290 and 310 mOsm.

15. The one-part aqueous intraocular irrigation solution according to claim 14 further including carbon dioxide in sufficient quantity to saturate the solution.

16. A method according to claim 14, wherein the storage stability of said one-part intraocular irrigating solution is at least 30 months.

17. A method of providing endothelium protection and corneal preservation in ocular therapy in mammals which comprises the administration of a one-part intraocular irrigating solution, characterized by storage stability for an extended period of time greater than 24 hours, and comprising:

(a) from 0.0001 grams per deciliter to 0.010 grams per deciliter of at least one gabaergic derivative having the general formula:

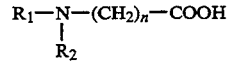

wherein:

n is from 1 to 5:

$R_1$ is hydrogen or $C_1$-$C_3$—straight chain alkyl;

$R_2$ is hydrogen or $C_1$-$C_{10}$—straight chain alkyl;

(b) from 0.0046 grams per deciliter to 10 grams per deciliter of an organic calcium salt of a non-heat labile complex sugar providing a source of energy compatible in aqueous solution with sodium bicarbonate; and (c) from 0.001 grams per deciliter to 10 grams per deciliter of an organic acid having the general formula:

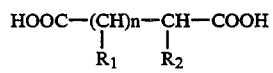

wherein:

n is between 1 and 3;
$R_1$ is a hydrogen atom of a hydroxyl group;
CH—$R_1$ may be replaced with C=O;
$R_2$ is a hydrogen or a hydroxyl;
the segment

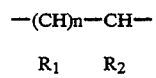

can be saturated or unsaturated; or lactic acid; or a pharmaceutically acceptable salt thereof;

(d) sodium chloride, potassium chloride, magnesium chloride, sodium bicarbonate, and sodium phosphate, in sufficient quantity to form an isotonic and stable aqueous solution.

18. The method of providing endothelium protection and cornea preservation according to claim 17 wherein carbon dioxide is provided in sufficient quantity to saturate the solution.

19. The method of providing endothelium protection and corneal preservation according to claim 17 in which the gabaergic derivative is aminocaproic acid, glycoll, dimethylglycine, sarcosine or gamma amino butyric acid.

20. The method of providing endothelium protection and corneal preservation according to claim 17 in which the acid specified under (c) is lactic acid or one of its pharmaceutically acceptable salts.

21. The method of providing endothelium protection and corneal preservation according to claim 17 wherein the solution is clear, stable under heat, sterile, and apyrongenic.

22. The method of providing endothelium protection and corneal preservation according to claim 17 wherein the solution has a pH between 6.8 and 7.6.

23. The method of providing endothelium protection and corneal preservation according to claim 17 wherein the solution has an osmolarity of between 290 and 310 mOsm.

24. The method of providing endothelium protection and corneal preservation according to claim 17 wherein $R_1$ in the formula under (a) is a $C_1$-$C_3$ alkyl group.

25. The method of providing endothelium protection and corneal preservation according to claim 17 wherein $R_2$ in the formula under (a) is an $C_1$-$C_{10}$ alkyl group.

26. The method of providing endothelium protection and corneal preservation according to claim 17 wherein the solution includes gamma aminobutyric acid, a lactic acid salt, the calcium salt of glucoheptonic acid and sodium bicarbonate.

27. The method of providing endothelium protection and corneal preservation according to claim 17 wherein the complex sugar is gluconic acid, glucoheptonic acid or glucono-glucoheptonic acid.

28. A method according to claim 26, wherein the storage stability of said one-part intraocular irrigating solution is at least 30 months.

29. A method of providing endothelium protection and corneal preservation in ocular surgery in mammals which comprises the administration of a one-part intraocular irrigating solution, characterized by its storage stability for an extended period of time greater than 24 hours, and comprising:

| | |
|---|---|
| Gamma amino butyric acid | 0.10 mg % to 10 mg % |
| Potassium chloride | 3.5 mg % to 50 mg % |
| Calcium glucoheptonate | 4.6 mg % to 80 mg % |
| Magnesium chloride (hexahydrate) | 1.5 mg % to 45 mg % |
| Sodium bicarbonate | 200 mg % to 300 mg % |
| Sodium acid phosphate (dihydrate) | 2.0 mg % to 8.0 mg % |
| Sodium lactate | 25 mg % to 150 mg % |
| Sodium chloride solution | 500 mg % to 800 mg % | each of the quantities being expressed in milligrams per deciliter, and wherein the pH of the solution is between 6.8 and 7.6 and the osmolarity is between 290 and 310 mOsm.

30. The method of providing endothelium protection and cornea preservation according to claim 29 wherein the solution contains carbon dioxide in sufficient quantities to saturate the solution.

* * * * *